United States Patent [19]

Reese

[11] Patent Number: 5,061,272
[45] Date of Patent: Oct. 29, 1991

[54] TONGUE CLEANER

[76] Inventor: Sandra C. Reese, 400 Central Park West, New York, N.Y. 10025

[21] Appl. No.: 536,948

[22] Filed: Jun. 11, 1990

Related U.S. Application Data

[63] Continuation of Ser. No. 220,026, Jul. 15, 1988, abandoned.

[51] Int. Cl.$^5$ .............................................. A61B 17/24
[52] U.S. Cl. ..................................... 606/161; 128/757
[58] Field of Search ................. 128/757; 606/160–162; 604/77; 30/324–328; 15/242

[56] References Cited

U.S. PATENT DOCUMENTS

| | | |
|---|---|---|
| 95,777 | 5/1835 | Peterkin . |
| 118,318 | 12/1839 | Fortunati . |
| 864,054 | 8/1907 | Abrams ................................. 606/161 |
| 1,533,123 | 4/1925 | Lewis . |
| 1,658,706 | 2/1928 | Carrott . |
| 1,741,143 | 12/1929 | Chin . |
| 1,811,775 | 6/1931 | Barkwill . |
| 1,860,924 | 5/1932 | Cooke . |
| 1,891,864 | 12/1932 | Barrett . |
| 1,907,737 | 5/1933 | Christie ................................. 30/328 |
| 2,049,956 | 8/1936 | Greenberg . |
| 2,405,029 | 7/1946 | Gallanty et al. ..................... 606/161 |
| 2,583,750 | 1/1952 | Runnels . |
| 2,708,762 | 5/1955 | Kling . |
| 3,477,435 | 11/1969 | Artelli . |
| 3,683,924 | 8/1972 | Louie . |
| 3,811,447 | 5/1974 | Weber . |
| 3,890,964 | 6/1975 | Castanedo . |
| 4,356,585 | 11/1982 | Protell et al. ........................ 606/161 |
| 4,455,704 | 6/1984 | Williams . |
| 4,488,327 | 12/1984 | Snider . |

FOREIGN PATENT DOCUMENTS 0537979  3/1922  France ................................. 606/161

Primary Examiner—C. Fred Rosenbaum
Assistant Examiner—William W. Lewis
Attorney, Agent, or Firm—Schechter, Brucker & Pavane

[57] ABSTRACT

A tongue cleaner comprises a handle and a scraping portion secured at one end to the handle, the scraping portion being curved, and in general conformity with a human tongue, and having an arc-shaped cross section defining a first channel on one side of the tongue cleaner for accumulating material scraped from the tongue.

2 Claims, 1 Drawing Sheet

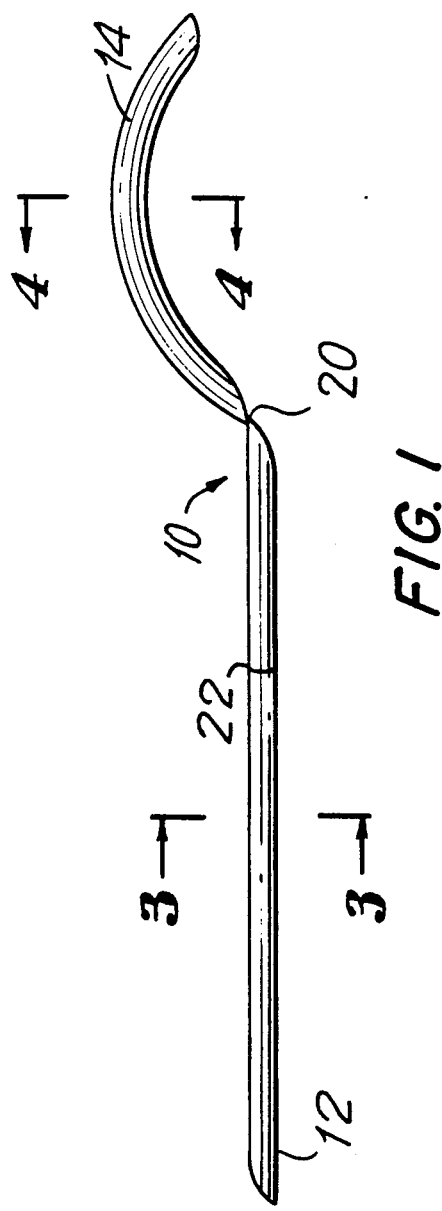
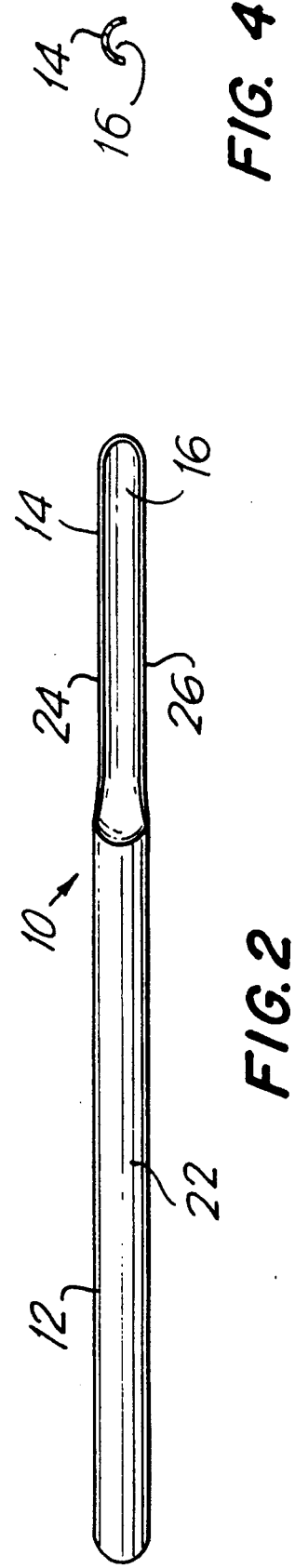

TONGUE CLEANER

This is a continuation of U.S. application Ser. No. 220,026, filed July 15, 1988, now abandoned.

BACKGROUND OF THE INVENTION

1. Field of the Invention

This invention pertains to tongue cleaners and more particularly to tongue cleaners of the type wherein cleaning is effected by scraping the surface of the tongue.

2. Prior Art

Brushing the teeth and flossing are widely accepted as basic oral hygiene. Cleaning of the tongue, however, is often overlooked. The tongue, like the teeth, may become coated with a film having an objectional odor, which may be particularly noticeable after sleep. Sometimes, the tongue surface acquires an unpleasant rough or furry feeling, which may be caused by saliva or mucus drying on the tongue as a result of breathing through the mouth. The best way to deal with these problems is by abrading or scraping the tongue surface to remove the agents responsible for the objectionable odor or feel.

To this end, some persons brush the surface of the tongue with a conventional tooth brush. More effective, however, are tongue scrapers specifically designed for scraping the surface of the tongue, and several such devices are suggested in the art.

For example, U.S. Pat. No. 3,477,435 discloses a tongue scraper comprising two curved surfaces joined at right angles. This device, however, does not incorporate a mechanism for trapping the material accumulated during the scraping operation, and incorporates a separately formed handle joined to the scraper, which adds to manufacturing expense.

U.S. Pat. No. 1,533,123 discloses a tongue scraper comprising a curved, slightly concave surface. While the curve generally conforms to the shape of the tongue, the slightly concave surface does not effectively trap matter accumulated during the scraping operation. Nor does the handle appear comfortable to grasp.

U.S. Pat. No. D95,777 discloses a toothbrush having a spoon-shaped member at one end, presumably for scraping the tongue. However, because the spoon is not curved, it cannot conform to the shape of the tongue, and therefore is less than fully effective for cleaning the surface thereof. U.S. Pat. Nos. 2,049,956, 2,708,762 and 4,356,585 also disclose toothbrushes having a tongue scraper at one end. In each case, however, the tongue scraper is not curved and therefore is less than fully effective for cleaning the tongue. U.S. Pat. No. 1,891,864 also discloses a tongue scraper comprising a flat edge.

U.S. Pat. No. 4,455,704 discloses yet another combined toothbrush and tongue scraper. However, because of the manner in which the tongue scraper extends from the toothbrush handle, holding the brush for scraping the tongue is awkward. Apparently in recognition of this fact, the tongue scraper is alternately disclosed as removable which, of course, adds to the expense of the device. A somewhat similar tongue scraper is disclosed in U.S. Pat. No. 1,811,775. Another combined toothbrush and tongue cleaner, wherein the tongue cleaner comprises a curved member at the end of the handle, is disclosed in U.S. Pat. No. 1,860,924. The curved portion is not, however, wide enough to conform with the shape of the tongue and is therefore less than fully effective. In addition, the interior of the curved section is flat, and consequently there is no mechanism for trapping matter accumulated during the scraping operation.

U.S. Pat. No. D118,318 discloses a tongue scraper in the form of a loop as does U.S. Pat. No. 4,488,327. It is not seen that these tongue scrapers will conform well with the upper surface of the tongue. Moreover, they do not include a mechanism for catching matter scraped from the tongue, other than the surfaces of the loop itself, from which such matter may readily drip off.

U.S. Pat. Nos. 3,683,924, 3,697,366 and 3,811,447 disclose generally U-shaped flexible scrapers. While these scrapers, because of their flexibility, can be formed to the shape of the surface of the tongue, they require two hands to use, and also do not incorporate a mechanism for trapping material accumulated during the scraping operation.

Still other scrapers, each of which suffers from one or more of the aforementioned drawbacks, are disclosed in U.S. Pat. Nos. 1,658,706; 1,741,143; 2,405,029; 2,583,750 and 3,890,964. In addition, various of the tongue cleaners referenced above are uncomfortable to grasp, and some, because of the number of parts, are relatively expensive to manufacturer.

Accordingly, it is an object of the present invention to provide an improved tongue cleaner which is effective for cleaning the surface of the tongue, and which incorporates a mechanism for accumulating matter removed from the tongue during the scraping operation.

It is a further object of the present invention to provide a tongue cleaner of the aforementioned type which is formed from a minimum number of parts for reducing manufacturing costs.

It is yet a further object of the present invention to provide a tongue cleaner of the aforementioned type which is comfortably grasped by both right and left handed users.

SUMMARY OF THE INVENTION

In accordance with the invention, I have invented a tongue cleaner which is inexpensive to manufacture, extremely effective for cleaning the tongue, and suitable for grasping by both right and left handed users.

In one embodiment, the tongue cleaner in accordance with the invention comprises a handle and a scraping portion secured at one end to the handle. The scraping portion is curved in general conformity with a human tongue and has a substantially semicircular cross section defining a first channel on one side of the tongue cleaner for accumulating matter scraped from the tongue.

In a preferred embodiment, the handle and scraping portion are integrally formed and the handle has a generally arc-shaped cross section defining a curved surface on said one side of the tongue cleaner and a second channel on the other side, such that the second channel and the curved surface of the handle serve as gripping surfaces for the thumb and other fingers, respectively, regardless of whether the user is right or left handed.

Further features and advantages of the tongue cleaner in accordance with the present invention will be more fully apparent from the following detailed description and annexed drawings of the presently preferred embodiment thereof.

BRIEF DESCRIPTION OF THE DRAWINGS

In the drawings:

FIG. 1 is a side view of the tongue cleaner in accordance with the present invention;

FIG. 2 is a bottom view of the tongue cleaner of FIG. 1;

FIG. 3 is a sectional view taken substantially along the line A—A in FIG. 1; and FIG. 4 is a sectional view taken substantially along the line B—B in FIG. 1.

DETAILED DESCRIPTION OF THE PREFERRED EMBODIMENT

Referring now to the drawings, the preferred tongue scraper in accordance with the present invention is generally designated at 10. As shown, the tongue scraper 10 is integrally formed, preferably from a strip of stainless steel.

The scraper 10 comprises a handle 12 and a scraping section 14. As best seen in FIGS. 1 and 4, and for reasons that will be explained below, the scraping section 14 is curved and has a generally semi-circular cross section defining a first channel 16 on one side of the scraper 10. As best seen in FIGS. 1, 2 and 4, the handle portion 12 is straight and has a generally arc-shape cross section defining a second channel 18 on the other side of the scraper 10 and a curved surface 22 on said one side.

To use the scraper 10, the scraper is grasped by the handle portion 12, preferably with the thumb in the channel 18 in the vicinity of the junction 20 between the handle portion 12 and the scraping portion 14, and with the other fingers wrapped about the curved surface 22. Because of the design of the scraper 10, it will be apparent that the scraper may be gripped in the foregoing fashion regardless of whether the user is right or left handed.

With the scraper 10 thus grasped, the scraping portion 14 is applied to the upper surface at the back of the tongue with the first channel 16 facing downward toward the tongue surface. As the upper surface of the tongue is curved, holding the scraper 10 in this fashion results in one of the edges 24, 26—depending upon whether the scraper 10 has been grasped with the right or left hand—contacting the upper surface of the tongue substantially along its entire width.

At this point, the scraper is moved forward such that the surface 24 or 26 scrapes the upper surface of the tongue for removing odor-causing and other objectionable matter, with any such matter accumulating in the first channel 16. Due to its semicircular shape, the channel 16 retains the accumulated matter and prevents it from dripping back onto the tongue as the scraping progresses. The scraper 10 may then be rinsed out as by hand or in a dishwasher, whereupon it is again ready for use.

From the foregoing, it will be apparent that the tongue scraper in accordance with the present invention is inexpensive to manufacture, extremely effective, and suitable for grasping by both right and left hand users.

While I have herein shown and described a preferred embodiment of the scraper of the present invention, it will be apparent to those of ordinary skill in the art that still further changes and modifications may be made therein without departing from the spirit and scope of the invention. Accordingly, the above description should be construed as illustrative and not in a limiting sense, the scope of the invention being defined by the following claims.

I claim:

1. A tongue cleaner comprising an integrally formed substantially rigid member defining a handle and a scraping portion, said handle and scraping portion being of substantially equal width, said scraping portion being curved in general conformity with a human tongue and having an arc-shaped cross section defining a first concave channel on one side of said tongue cleaner, said handle also having a generally arc-shaped cross section defining a convex surface on said one side of said tongue cleaner and a second concave channel on the other side thereof, whereby said second channel and said convex surface serve as gripping surfaces for the thumb and other fingers, respectively, for both right and left handed users.

2. The tongue cleaner according to claim 1, wherein said scraping portion has a generally semicircular cross section.

* * * * *